United States Patent
Wang et al.

(10) Patent No.: US 12,391,994 B2
(45) Date of Patent: Aug. 19, 2025

(54) REAGENT KIT AND MARKERS FOR DETECTING RENAL CELL CARCINOMA AND METHOD THEREOF

(71) Applicant: Hangzhou York Biotech Co., LTD., Hangzhou (CN)

(72) Inventors: Junhong Wang, Hangzhou (CN); Qingxia Jiang, Hangzhou (CN); Huijia Meng, Hangzhou (CN)

(73) Assignee: Hangzhou York Biotech Co., LTD., Hangzhou (CN)

(*) Notice: Subject to any disclaimer, the term of this patent is extended or adjusted under 35 U.S.C. 154(b) by 654 days.

(21) Appl. No.: 17/841,253

(22) Filed: Jun. 15, 2022

(65) Prior Publication Data
US 2023/0092109 A1    Mar. 23, 2023

(30) Foreign Application Priority Data
Jun. 18, 2021 (CN) .......................... 202110674617.1

(51) Int. Cl.
| | |
|---|---|
| *C12Q 1/6886* | (2018.01) |
| *C12Q 1/6851* | (2018.01) |
| *G16H 50/20* | (2018.01) |
| *G16H 50/30* | (2018.01) |
| *C12Q 1/6806* | (2018.01) |

(52) U.S. Cl.
CPC ......... *C12Q 1/6886* (2013.01); *C12Q 1/6851* (2013.01); *G16H 50/20* (2018.01); *G16H 50/30* (2018.01); *C12Q 1/6806* (2013.01); *C12Q 2600/158* (2013.01); *C12Q 2600/16* (2013.01); *C12Q 2600/178* (2013.01)

(58) Field of Classification Search
CPC ............... C12Q 1/6886; C12Q 1/6806; C12Q 2600/158; C12Q 2600/178; C12Q 2600/16; C12Q 1/6851; G16H 50/20; G16H 50/30
See application file for complete search history.

(56) References Cited

FOREIGN PATENT DOCUMENTS
WO   WO-2006133022 A2 * 12/2006 ........... C12N 15/113
* cited by examiner

*Primary Examiner* — Anne M. Gussow
*Assistant Examiner* — Emma R Hoppe
(74) *Attorney, Agent, or Firm* — ANOVA LAW GROUP, PLLC

(57) ABSTRACT

Embodiments of the present disclosure provide a reagent kit and a method for detecting renal cell carcinoma. The reagent kit includes a set of primer-probe mixes for detecting miRNAs in exosomes. The set of primer-probe mixes includes a reverse transcription primer R-23b for a specific reverse transcription miR-23b-5p target, a universal forward primer Ge—F, a specific reverse primer 23b-R, and a specific probe 23b-P; a reverse transcription primer R-34c for a specific reverse transcription miR-34c-5p target, a universal forward primer Ge—F, a specific reverse primer 34c-R, and a specific probe 34c-P; a reverse transcription primer R-210 for a specific reverse transcription miR-210-3p target, a universal forward primers Ge—F f, a specific reverse primer 210-R, and a specific probe 210-P; and a reverse transcription primer R-508 for a specific reverse transcription miR-508-3p target, a universal forward primer Ge—F, a specific reverse primer 508-R, and a specific probe 508-P.

5 Claims, 3 Drawing Sheets
Specification includes a Sequence Listing.

REAGENT KIT AND MARKERS FOR DETECTING RENAL CELL CARCINOMA AND METHOD THEREOF

REFERENCE TO AN ELECTRONIC SEQUENCE LISTING

The contents of the electronic sequence listing (313SEQL_ST25.txt; Size: 3 kilobytes; and Date of Creation: Nov. 11, 2022) are herein incorporated by reference in its entirety.

CROSS-REFERENCE TO RELATED APPLICATION

This application claims the priority of Chinese Patent Application No. 202110674617.1, filed on Jun. 18, 2021, the content of which is incorporated herein by reference in its entirety.

TECHNICAL FIELD

The present disclosure generally relates to the field of preparation of renal cell carcinoma markers and, more particularly, relates to a reagent kit and markers for detecting renal cell carcinoma and a method thereof.

BACKGROUND

Renal cell carcinoma (RCC), referred to as renal cancer, is one of the most common tumors. Renal cancer ranks second in urogenital tumors in China, which is only less than bladder tumor and accounts for about 3% of adult malignant tumors. Renal cancer is also a highly malignant tumor in the urinary system, which is not sensitive to radiotherapy and chemotherapy. Currently, surgical resection is still the only effective manner for treatment of renal cancer, but 20% to 40% of patients still experience recurrence after surgery, with mortality rate higher than 40%. Moreover, rumor markers are lacked for early diagnosis of renal cancer. There is an urgent need to search for new and effective tumor markers for diagnosis and treatment of renal cancer.

Currently, clinical detection manners for renal cancer may mainly rely on urine occult blood test, biochemical examination, and imaging manners including MRI and CT scans, which have obvious limitations. Urine occult blood test for RCC may be mostly based on detection of a small amount of blood in the urine. However, in a variety of cases, the symptom of hematuria may only appear when the kidney tumor reaches a considerable extent, such that urine occult blood test may have low sensitivity. Biochemical examination may lack specificity and only reflect general body situation, thereby being difficult to clearly identify renal cancer. In addition, imaging examination, having relatively high price, may be difficult to detect early renal cancer tumors, and require large instruments for examination with cumbersome operations.

Exosomes are small vesicles of 30-150 nm in size that are secreted by living cells. Exosomes secreted by renal tumor cells, which are important media of information transfer with external cells, play an important role in occurrence, progression, metastasis and drug resistance of renal tumors by carrying and delivering biologically active substances (such as miRNA, lncRNA and proteins). Basic information of cancer cells may be directly obtained by analyzing exosomes without genomic background interference. Therefore, exosomes and their contents have become novel biomarkers for early diagnosis of renal cancer.

MicroRNAs (i.e., miRNAs) are a class of endogenous non-coding small molecule single-stranded RNAs, which may be about 19-25 nucleotides in length and regulate post-transcriptional level gene expression. miRNAs may bind to their target mRNAs through complementary base pairing in the 3'-terminal non-coding regions (3'UTR) of their target mRNAs, causing translation inhibition and/or degradation of target mRNAs. miRNAs may regulate a variety of key cellular behaviors including cell proliferation, differentiation, cycle and tumor formation. In recent years, a large number of studies have shown that abnormal expression of miRNAs often occurs in tumors, and some miRNAs may have tumor suppressing or carcinogenic effects. Due to tissue and disease specific expression properties of miRNAs in exosomes and their desirable regulatory potential, exosomal miRNAs have been considered to have potential to become new and effective tumor markers.

SUMMARY

One aspect of the present disclosure provides a reagent kit for detecting renal cell carcinoma. The reagent kit includes a set of primer-probe mixes for detecting miRNAs in exosomes. The set of primer-probe mixes includes a reverse transcription primer R-23b for a specific reverse transcription miR-23b-5p target, a universal forward primer Ge—F for fluorescent PCR (polymerase chain reaction) detection, a specific reverse primer 23b-R, and a specific probe 23b-P; a reverse transcription primer R-34c for a specific reverse transcription miR-34c-5p target, a universal forward primer Ge—F for fluorescent PCR detection, a specific reverse primer 34c-R, and a specific probe 34c-P; a reverse transcription primer R-210 for a specific reverse transcription miR-210-3p target, a universal forward primers Ge—F for fluorescent PCR detection, a specific reverse primer 210-R, and a specific probe 210-P; and a reverse transcription primer R-508 for a specific reverse transcription miR-508-3p target, a universal forward primer Ge—F for fluorescent PCR detection, a specific reverse primer 508-R, and a specific probe 508-P. The set of primer-probe mixes includes

```
R-23b (SEQ ID NO: 1):
5'-GTGCTAAGCACAGCAGGGTCCGAGGTATTCGCTGTGCTTA
GCACGTGGTA-3';

R-34c (SEQ ID NO: 2):
5'-CACGATTCGTGAGCAGGGTCCGAGGTATTCGCTCACGAAT
CGTGGCAATC-3';

R-210 (SEQ ID NO: 3):
5'-TGCATCAGATGTGCAGGGTCCGAGGTATTCGCACATCTGA
TGCATCAGCC-3';

R-508 (SEQ ID NO: 4):
5-CGTACAGTCCAGGCAGGGTCCGAGGTATTCGCCTGGACTGT
ACGTCTACTC-3';

Ge-F (SEQ ID NO: 5):
5'-GCAGGGTCCGAGGTATTC-3';

23b-R (SEQ ID NO: 6):
5'-CATCACATTGCCAGGGAT-3';
```

-continued

```
34c-R (SEQ ID NO: 7):
5'-GCAGGCAGTGTAGTTAGCT-3';

210-R (SEQ ID NO: 8):
5'-GGCTGTGCGTGTGACAGC-3';

508-R (SEQ ID NO: 9):
5'-GCTGATTGTAGCCTTTTG-3';

23b-P (SEQ ID NO: 10):
5'FAM-ACCACGTGCTAAGCACAG-MGB 3';

34c-P (SEQ ID NO: 11):
5'VIC-GATTGCCACGATTCGTGAGC-MGB3';

210-P (SEQ ID NO: 12):
5'ROX-GCTGATGCATCAGATGTG-MGB 3';
and

508-P (SEQ ID NO: 13):
5'CY5-AGTAGACGTACAGTCCAGG-MGB 3'.
```

Another aspect of the present disclosure provides a method for detecting renal cell carcinoma. The method includes preparing a reagent kit for detecting renal cell carcinoma, where the reagent kit includes a set of primer-probe mixes for detecting miRNAs in exosomes. The set of primer-probe mixes includes a reverse transcription primer R-23b for a specific reverse transcription miR-23b-5p target, a universal forward primer Ge—F for fluorescent PCR (polymerase chain reaction) detection, a specific reverse primer 23b-R, and a specific probe 23b-P; a reverse transcription primer R-34c for a specific reverse transcription miR-34c-5p target, a universal forward primer Ge—F for fluorescent PCR detection, a specific reverse primer 34c-R, and a specific probe 34c-P; a reverse transcription primer R-210 for a specific reverse transcription miR-210-3p target, a universal forward primers Ge—F for fluorescent PCR detection, a specific reverse primer 210-R, and a specific probe 210-P; and a reverse transcription primer R-508 for a specific reverse transcription miR-508-3p target, a universal forward primer Ge—F for fluorescent PCR detection, a specific reverse primer 508-R, and a specific probe 508-P. The set of primer-probe mixes includes

```
R-23b (SEQ ID NO: 1):
5'-GTGCTAAGCACAGCAGGGTCCGAGGTATTCGCTGTGCTTA

GCACGTGGTA-3';

R-34c (SEQ ID NO: 2):
5'-CACGATTCGTGAGCAGGGTCCGAGGTATTCGCTCACGAAT

CGTGGCAATC-3';

R-210 (SEQ ID NO: 3):
5'-TGCATCAGATGTGCAGGGTCCGAGGTATTCGCACATCTGA

TGCATCAGCC-3';

R-508 (SEQ ID NO: 4):
5-CGTACAGTCCAGGCAGGGTCCGAGGTATTCGCCTGGACTGT

ACGTCTACTC-3';

Ge-F (SEQ ID NO: 5):
5'-GCAGGGTCCGAGGTATTC-3';

23b-R (SEQ ID NO: 6):
5'-CATCACATTGCCAGGGAT-3';

34c-R (SEQ ID NO: 7):
5'-GCAGGCAGTGTAGTTAGCT-3';
```

```
210-R (SEQ ID NO: 8):
5'-GGCTGTGCGTGTGACAGC-3';

508-R (SEQ ID NO: 9):
5'-GCTGATTGTAGCCTTTTG-3';

23b-P (SEQ ID NO: 10):
5'FAM-ACCACGTGCTAAGCACAG-MGB 3';

34c-P (SEQ ID NO: 11):
5'VIC-GATTGCCACGATTCGTGAGC-MGB3';

210-P (SEQ ID NO: 12):
5'ROX-GCTGATGCATCAGATGTG-MGB 3';
and

508-P (SEQ ID NO: 13):
5'CY5-AGTAGACGTACAGTCCAGG-MGB 3'.
```

The method further includes obtaining a Mi-Score based on a combined application determination formula: Mi-Score=$1/[1+\exp(-z)]$, and a parameter $z=52.3-0.18*A-0.33*B-0.79*C-0.76*D$, where A is a Ct value of miR-23b-5p detection, B is a Ct value of miR-34c-5p detection, C is a Ct value of miR-210-3p detection, and D is a Ct value of miR-508-3p detection; and indicating that a subject has a higher risk of renal cancer when the Mi-Score is greater than 0.65, and indicating that a subject has a lower risk of renal cancer when the Mi-Score is less than 0.65.

Other aspects of the present disclosure can be understood by those skilled in the art in light of the description, the claims, and the drawings of the present disclosure.

BRIEF DESCRIPTION OF THE DRAWINGS

The accompanying drawings, which are incorporated into a part of the specification, illustrate embodiments of the present disclosure and together with the description to explain the principles of the present disclosure.

DETAILED DESCRIPTION

Figure 1:
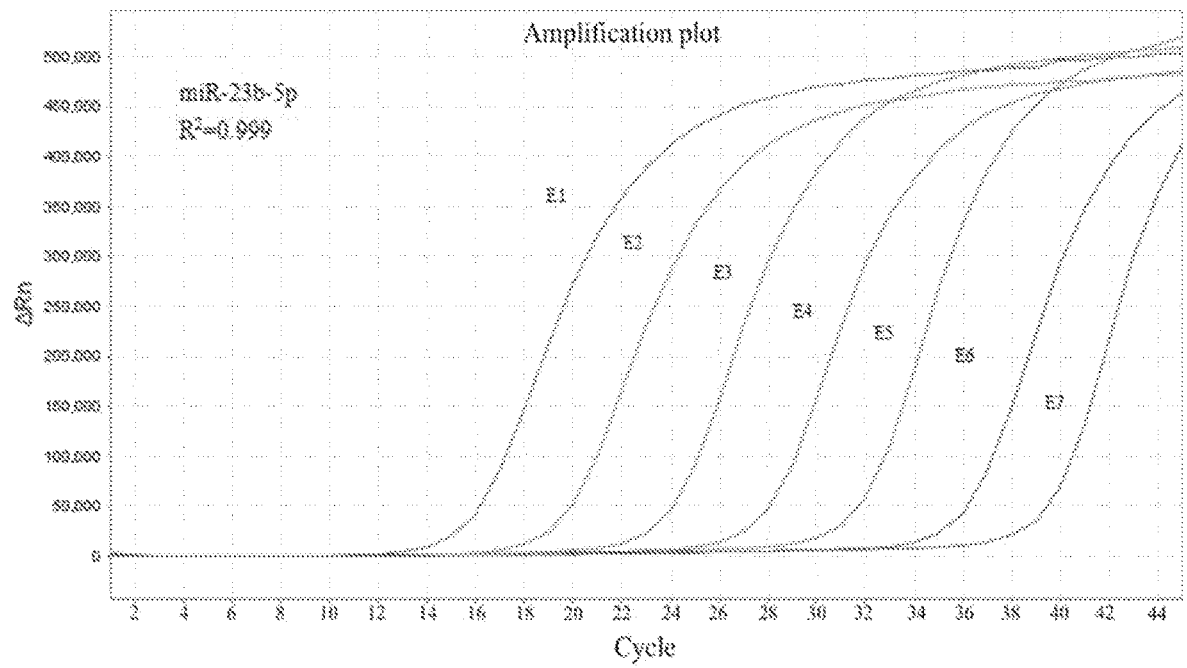
FIG. 1 illustrates a miR-23b-5p target amplification plot of renal cancer exosomal miRNA detection.
Figure 2:
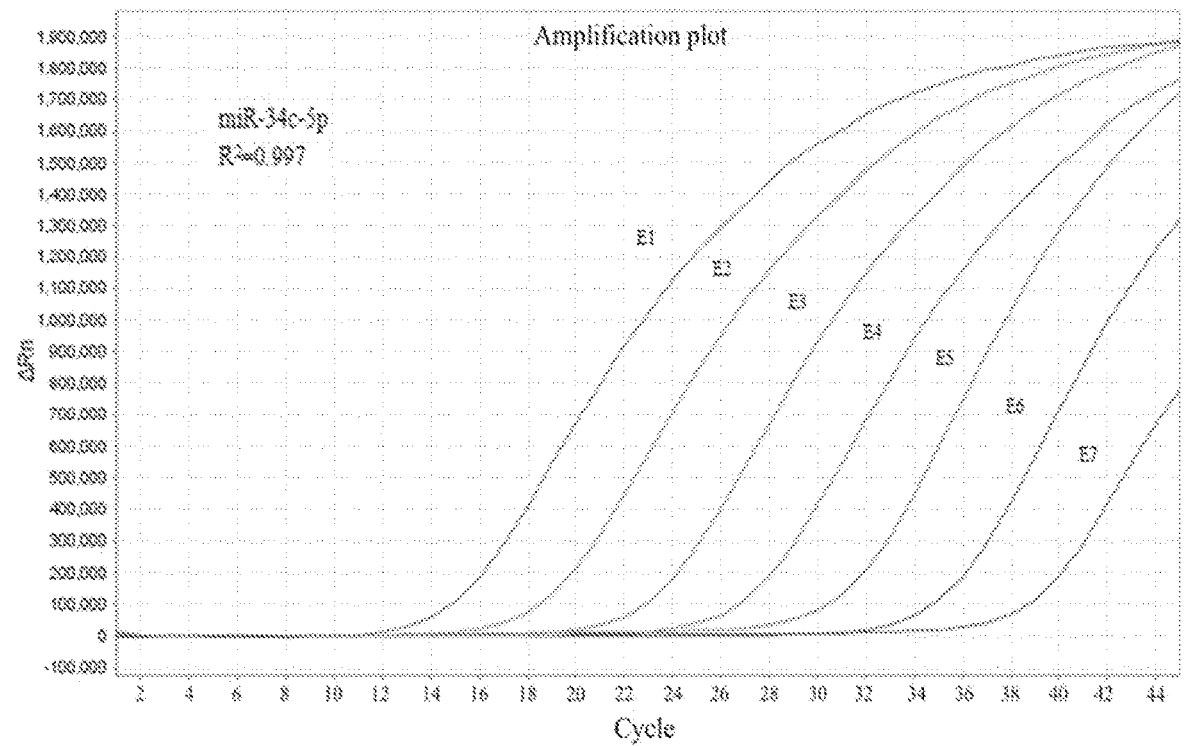
FIG. 2 illustrates a miR-34c-5p target amplification plot of renal cancer exosomal miRNA detection.
Figure 3:
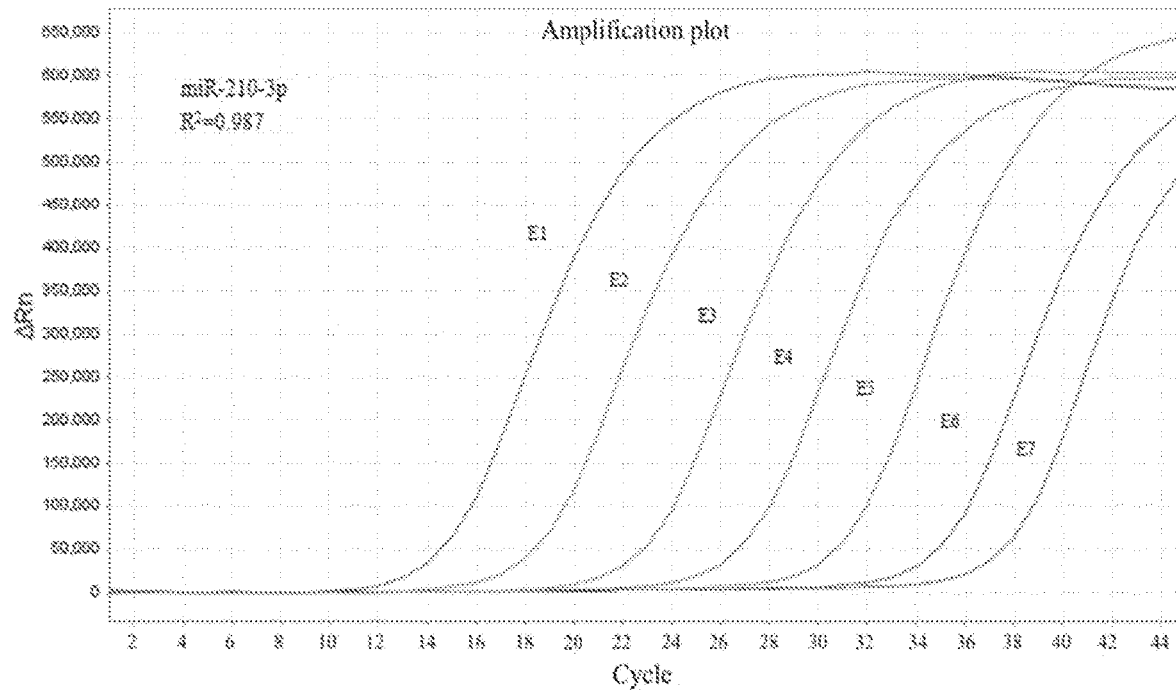
FIG. 3 illustrates an miR-210-3p target amplification plot of renal cancer exosomal miRNA detection.
Figure 4:
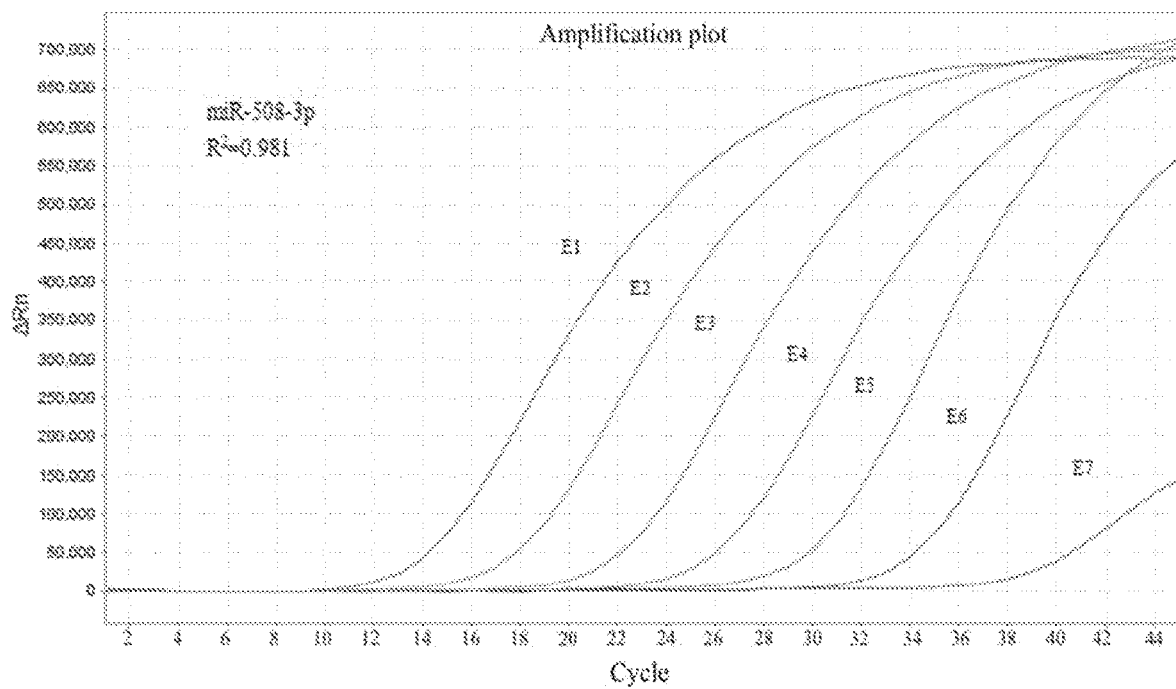
FIG. 4 illustrates an miR-508-3p target amplification plot of renal cancer exosomal miRNA detection.

Technical solutions of the present disclosure are further described in detail below through examples and in conjunction with accompanying drawings.

The present disclosure relates to the field of preparation of renal cell carcinoma markers and, more particularly, relates to an application of a set of primer-probe mixes in preparing renal cell carcinoma markers and a reagent kit. The combination of miR-23b-5p, miR-34c-5p, miR-210-3p, miR-508-3p is applied in exosomes in the preparation of diagnostic and predictive prostate cancer markers. The method uses the TaqMan fluorescent RT-PCR (reverse transcription-polymerase chain reaction) manner to detect exosomal miRNA targets including miR-23b-5p, miR-34c-5p, miR-210-3p and miR-508-3p in a single tube. According to Ct values obtained after detection, the probability calculation formula of renal cancer occurrence is obtained by binary Logistic linear regression fitting. The reagent kit has the advantages of simple sampling, simple operation, short time, high efficiency and practicality, and objective results; and its clinical performance is better than existing renal cancer diagnosis technology, thereby having a desirable application prospect.

Exemplary embodiment 1: the composition of the reagent kit

In one embodiment, the renal cancer exosomal miRNA detection reagent kit may include a reagent for preparing reverse transcription reaction system, a primer-probe mix reagent and a PCR reagent for preparing a PCR system, and positive and negative controls for quality control testing process.

1) The reverse transcription reagent may be 5×AMV RT (avian myeloblastosis virus reverse transcriptase) buffer, which may include AMV RT (10 U/μl), 0.05 μM R-23b, 0.05 μM R-34c, 0.05 μM R-210, 0.05 μM R-508, 250 mM Tris-HCl (pH 8.3), 250 mM KCl, 50 mM $MgCl_2$, 2.5 mM spermine, 50 mM DTT (dithiothreitol), and 2.5 mM dNTP (deoxynucleotide triphosphate).

2) The composition of the primer-probe mix reagent may include 1 μM Ge—F, 0.25 μM 23b-R, 0.25 μM 34c-R, 0.25 μM 210-R, 0.25 μM 508-R, 0.25 μM 23b-P, 0.25 μM 34c-P, 0.25 μM 210-P, and 0.25 μM 508-P.

3) The PCR reagent may be 2×PCR buffer, which may include Taq (*T. aquaticus*) DNA polymerase (2 U/μl), 200 mmol/L Tris-HCl (pH 8.3), 60 mmol/L $MgCl_2$, 350 mmol/L KCl, 2.5 mmol/L DTT, and 5 mM dNTP.

4) The positive control may be combination of synthetic miRNA mimic fragments. The composition, concentration and sequence of the positive control may include:

```
0.1 pg/mL miR-23b-5p mimics
(5'-AUCACAUUGCCAGGGAUUACCAC-3'), 0.1 pg/mLmiR-34c-5p mimics
(5'-AGGCAGUGUAGUUAGCUGAUUGC-3'), 0.1 pg/mLmiR-210-3p mimics
(5'-CUGUGCGUGUGACAGCGGCUGA-3),
and 0.1 pg/mLmiR-508-3p mimics
(5'-UGAUUGUAGCCUUUUGGAGUAGA-3').
```

5) The negative control may be ultrapure water for sub-packaging.

Exemplary embodiment 2: standard material preparation and linearity verification 1) the Composition, Concentration and Sequence of Synthetic miRNA Mimic Fragments May Include:

```
10 pg/mL miR-23b-5p mimics
(5'-AUCACAUUGCCAGGGAUUACCAC-3'), 10 pg/mLmiR-34c-5p mimics
(5'-AGGCAGUGUAGUUAGCUGAUUGC-3'), 10 pg/mLmiR-210-3p mimics
(5'-CUGUGCGUGUGACAGCGGCUGA-3'),
and 10 pg/mLmiR-508-3p mimics
(5'-UGAUUGUAGCCUUUUGGAGUAGA-3').
```

The high-concentration miRNA standard material E1 may be prepared according to above-mentioned components with thorough mixing. E1 may be taken as the stock solution to be diluted with ultrapure water for 10-fold to obtain E2. Similarly, a 10-fold dilution gradient may be used to perform a total of 6 dilutions, and total 7 concentrations of standard materials of E1, E2, E3, E4, E5, E6, and E7 may be obtained, respectively.

Reverse transcription may be performed using the following formula shown in Table 1.

TABLE 1

| Component | Volume |
| --- | --- |
| Standard material | 8 μL |
| Reverse transcription reagent | 2 μL |

2) Fluorescent PCR Detection

After the preparation is completed, incubation may be performed at a constant temperature of 16° C. for 30 min, and cDNA fragments with extended sequences may be obtained after reverse transcription. After reverse transcription is completed, fluorescent PCR amplification may be performed according to the following formula shown in Table 2.

TABLE 2

| Component | Volume |
| --- | --- |
| cDNA | 10 μL |
| Primer-probe mix reagent | 5 μL |
| PCR reagent | 15 μL |

After the preparation is completed, PCR detection may be performed using the following procedure, where corresponding procedure parameters are shown in Table 3.

TABLE 3

| Temperature | Time | Number of cycles |
| --- | --- | --- |
| 95° C. | 10 min | 1 cycle |
| 95° C. | 10 s | 45 cycles |
| 60° C. | 30 s (fluorescence collection) | |

As the results shown in FIGS. 1 to 4, the fluorescence curves of four channels of miR-23b-5p, miR-34c-5p, miR-210-3p, and miR-508-3p may all show standard S shapes, and the linear correlation coefficients r may be 0.999, 0.997, 0.987, 0.981, respectively, showing a desirable linear relationship. It demonstrates that multiplex reverse transcription quantitative PCR (RT-qPCR) established in the present disclosure may have desirable analysis and detection performance in detection of mimic miRNA samples.

Exemplary embodiment 3: renal cancer exosomal miRNA detection using urine samples 1) Exosomal miRNA Extraction and Reverse Transcription of Urine Samples About 5 mL of a subject's urine may be collected; the exoEasy Maxi Kit (QIAGEN, CAT: 76064), which may include 20 vesicle preps containing 20 exoEasy maxi spin columns, collection tubes (50 ml) and the like, may be used to extract exosomes in the urine; and the Universal microRNA Purification Kit (EZ Bioscience, CAT: EZB-miRN1) may be used to extract miRNA extract in exosomes. Reverse transcription may be performed using the following formula shown in Table 4.

TABLE 4

| Component | Volume |
| --- | --- |
| Urine miRNA extract/control | 8 μL |
| Reverse transcription reagent | 2 μL |

2) Fluorescent PCR Detection:

After the preparation is completed, incubation may be performed at a constant temperature of 16° C. for 30 min, and cDNA fragments with extended sequences may be obtained after reverse transcription. After reverse transcription is completed, fluorescent PCR amplification may be performed according to the following formula shown in Table 5.

TABLE 5

| Component | Volume |
| --- | --- |
| cDNA | 10 μL |
| Primer-probe mix reagent | 5 μL |
| PCR reagent | 15 μL |

After the preparation is completed, PCR detection may be performed using the following procedure, where corresponding procedure parameters are shown in Table 6.

TABLE 6

| Temperature | Time | Number of cycles |
| --- | --- | --- |
| 95° C. | 10 min | 1 cycle |
| 95° C. | 10 s | 45 cycles |
| 60° C. | 30 s (fluorescence collection) | |

3) Substitution into Regression Formula and Result Interpretation

According to the detection result of fluorescent PCR, the result may be substituted into the following formula: Mi-Score=$1/[1+\exp(-z)]$, and a parameter $z=52.3-0.18*A-0.33*B-0.79*C-0.76*D$, where A is the Ct value of miR-23b-5p detection, B is the Ct value of miR-34c-5p detection, C is the Ct value of miR-210-3p detection, and D is the Ct value of miR-508-3p detection. When detected Mi-Score is greater than 0.65, it indicates that the subject may have a higher risk of developing renal cancer; and when detected Mi-Score is less than 0.65, it indicates that the subject may have a lower risk of developing renal cancer.

Exemplary embodiment 4: clinical sample experiment 1 (training set)

Figure 5:
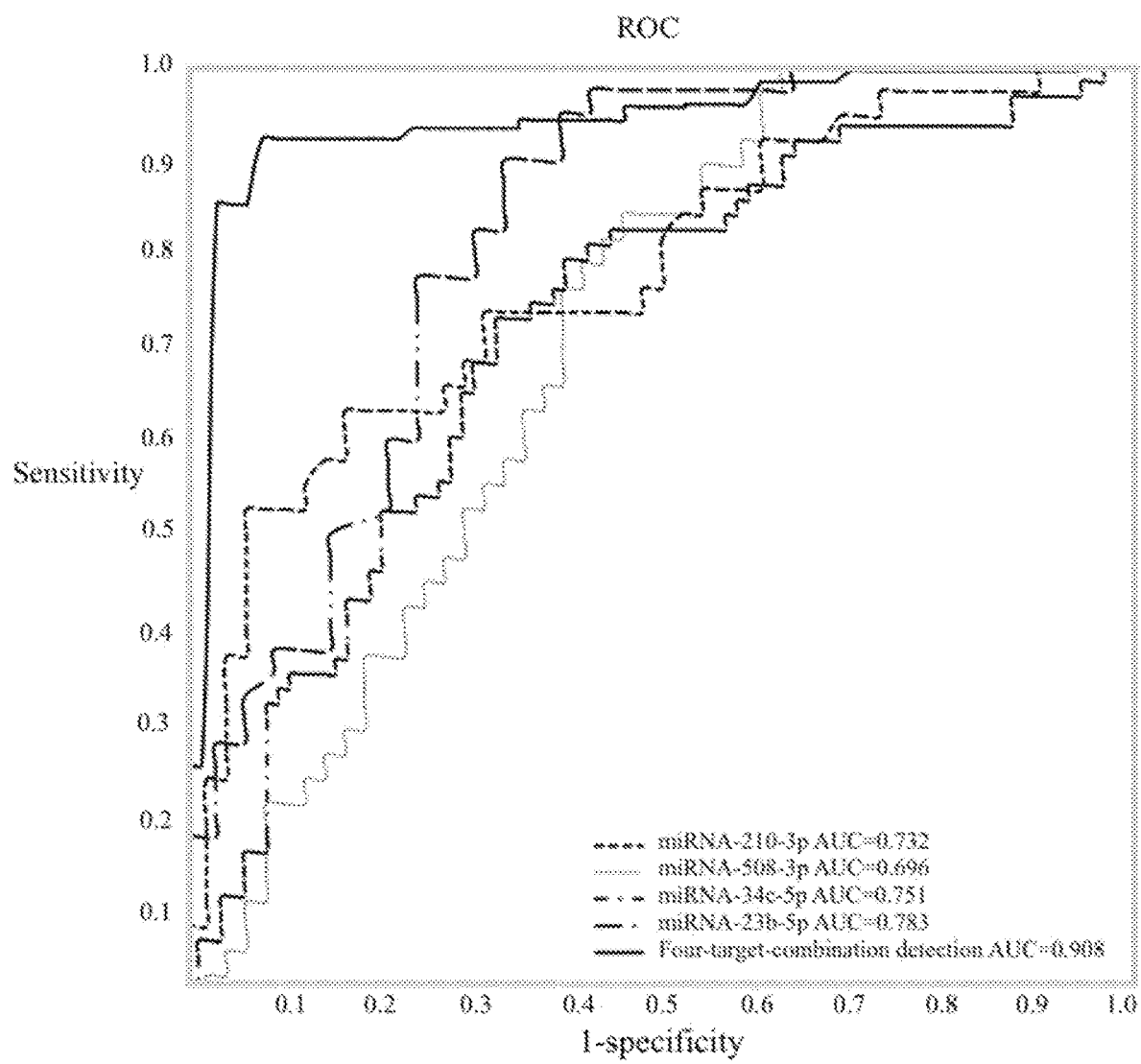
FIG. 5 illustrates a comparison of AUC value based on ROC (receiver operating characteristic) curves of multi-target-combination index detection and single target index detection.

The urine samples of 247 patients who were ready to undergo renal biopsy were collected from the First Affiliated Hospital of Zhejiang University for implementation. Four miRNA targets of miR-23b-5p, miR-34c-5p, miR-210-3p and miR-508-3p in urinary exosomes were detected simultaneously, and Mi-Score was calculated. Taking the result of renal biopsy as the gold standard (113 cases of renal cancer and 134 cases of non-renal cancer in 247 samples), the logistic regression model may be used to calculate the combined determination formula of all miRNAs, and the ROC (receiver operating characteristic) curve may be drawn (as shown in FIG. 5). The final formula of the Mi-Score may be Mi-Score=$1/[1+\exp(-z)]$, and a parameter $z=52.3-0.18*A-0.33*B-0.79*C-0.76*D$, where A is the Ct value of miR-23b-5p detection, B is the Ct value of miR-34c-5p detection, C is the Ct value of miR-210-3p detection, and D is the Ct value of miR-508-3p detection. Meanwhile, using the result of renal biopsy as the gold standard and the Ct value detected by a single exosomal miRNA as a variable, the ROC curve may be drawn (as shown in FIG. 5). Comparing the performance of the multi-target (e.g., four-target) combination detection with the performance of the single target detection, it is found that, AUC (area under curve) values may be the following: combination detection (AUC=0.908)>miR-23b-5p (AUC=0.783)>miR-34c-5p (AUC=0.751)>miR-210-3p (AUC=0.732)>miR-508-3p (AUC=0.696). According to the ROC curves, when the sensitivity is near 90%, specificity and other data of each detection system are compared and summarized in Table 7 below.

TABLE 7

| Target detection | AUC | Sensitivity | Specificity |
| --- | --- | --- | --- |
| Combination detection | 0.908 | 92.3% | 93.4% |
| miR-23b-5p | 0.783 | 90.2% | 60.4% |
| miR-34c-5p | 0.751 | 91.1% | 52.9% |
| miR-210-3p | 0.732 | 90.7% | 50.8% |
| miR-508-3p | 0.696 | 88.0% | 47.2% |

Exemplary embodiment 5: clinical sample experiment 2 (testing set)

The urine samples of 132 patients who were ready to undergo renal biopsy were collected from the First Affiliated Hospital of Zhejiang University for implementation. Meanwhile, according to exemplary embodiment 3, targets of miR-23b-5p, miR-34c-5p, miR-210-3p, and miR-508-3p in the exosomes in urine were detected, and Mi-Score was calculated. Taking the result of renal biopsy as the gold standard (67 cases of renal cancer and 65 cases of non-renal cancer in 132 samples), a two-way table may be drawn; and the data of sensitivity, specificity, negative predictive value, positive predictive value and the like of exosomal miRNA for renal cancer detection (Table 8) may be calculated. Meanwhile, diagnostic information of CT scan images for a total of 109 cases was collected. Taking renal biopsy as the gold standard, the sensitivity, specificity, negative predictive value, and positive predictive value of CT detection of renal cancer (Table 9) may be calculated. Through detection performance comparison between renal cancer miRNA detection and CT detection, it is found that detection performance of renal cancer miRNA may be significantly desirable than detection performance of CT scan images (Table 9), which may indicate that renal cancer exosomal miRNA may have excellent detection performance. Combined with advantages of simple sampling, simple operation, short time and low cost, renal cancer exosomal miRNA detection may have broad application prospects.

TABLE 8

| Renal cancer exosomal miRNA detection | Renal biopsy | | Total |
| --- | --- | --- | --- |
| | Positive | Negative | |
| Positive | 63 | 3 | 66 |
| Negative | 4 | 62 | 66 |
| Total | 67 | 65 | 132 |

TABLE 9

| Performance index | Renal cancer miRNA detection | CT scan image diagnosis |
| --- | --- | --- |
| Sensitivity | 94.0% | 82.1% |
| Specificity | 95.4% | 76.9% |
| Positive predictive value | 95.5% | 78.6% |
| Negative predictive value | 93.9% | 80.6% |
| Compliance rate | 94.7% | 79.5% |

Sequence

Reverse transcription primers and probes may include:

R-23b (SEQ ID NO: 1):
5'-GTGCTAAGCACAGCAGGGTCCGAGGTATTCGCTGTGCTTA
GCACGTGGTA-3',

R-34c (SEQ ID NO: 2):
5'-CACGATTCGTGAGCAGGGTCCGAGGTATTCGCTCACGAAT
CGTGGCAATC-3',

R-210 (SEQ ID NO: 3):
5'-TGCATCAGATGTGCAGGGTCCGAGGTATTCGCACATCTGA
TGCATCAGCC-3',

R-508 (SEQ ID NO: 4):
5-CGTACAGTCCAGGCAGGGTCCGAGGTATTCGCCTGGACTGT
ACGTCTACTC-3',

Ge-F (SEQ ID NO: 5):
5'-GCAGGGTCCGAGGTATTC-3',

23b-R (SEQ ID NO: 6):
5'-CATCACATTGCCAGGGAT-3',

34c-R (SEQ ID NO: 7):
5'-GCAGGCAGTGTAGTTAGCT-3',

210-R (SEQ ID NO: 8):
5'-GGCTGTGCGTGTGACAGC-3',

508-R (SEQ ID NO: 9):
5'-GCTGATTGTAGCCTTTTG-3',

23b-P (SEQ ID NO: 10):
5'FAM-ACCACGTGCTAAGCACAG-MGB 3',

34c-P (SEQ ID NO: 11):
5'VIC-GATTGCCACGATTCGTGAGC-MGB3',

210-P (SEQ ID NO: 12):
5'ROX-GCTGATGCATCAGATGTG-MGB 3',
and

508-P (SEQ ID NO: 13):
5'CY5-AGTAGACGTACAGTCCAGG-MGB 3'.

From above-mentioned embodiments, it may be seen that the solutions provided by the present disclosure may achieve at least the following beneficial effects.

The present disclosure provides an exosomal miRNA detection kit which is fast, convenient, and high in accuracy, and realizes early auxiliary diagnosis of renal cancer, and provides the combined use of miR-23b-5p, miR-34c-5p, miR-210-3p, miR-508-3p in exosomes as a renal cancer molecular marker.

The present disclosure provides a kit for the combined detection of renal cancer with miR-23b-5p, miR-34c-5p, miR-210-3p, and miR-508-3p exosomes of urine. The kit uses multiplex qRT-PCR technology to simultaneously detect four markers of miR-23b-5p, miR-34c-5p, miR-210-3p and miR-508-3p in exosomes in one urine sample. Furthermore, miRNA positive and negative controls have been developed to control entire detection process of the kit. The positive control may be synthetic miRNA mixtures, and the negative control may be ultrapure water.

One objective of the present disclosure is to provide a combined application of miR-23b-5p, miR-34c-5p, miR-210-3p and miR-508-3p in exosomes in the preparation of markers for diagnosis and prediction of prostate cancer. The method may use the Taqman fluorescence RT-PCR manner to detect the exosomal miRNA targets miR-23b-5p, miR-34c-5p, miR-210-3p, miR-508-3p in a single tube; and according to the Ct values obtained after detection, the calculation formula of the probability of occurrence of renal cancer may be obtained by binary Logistic linear regression fitting.

The present disclosure provides a set of miRNA targets in renal cancer exosomes for combined detection. The targets may include miR-23b-5p, miR-34c-5p, miR-210-3p, and miR-508-3p, and a Logistic regression model may be established with such four targets. The model can obtain the risk index Mi-Score of renal cancer, which can be used as an indicator for early diagnosis of renal cancer, thereby improving assay performance for diagnosing and predicting kidney cancer.

Moreover, the present disclosure also provides a detection kit based on above-mentioned solutions and corresponding application. The kit may have the advantages of simple sampling, simple operation, short time, high efficiency and practicality, and objective results; and its clinical performance is better than existing renal cancer diagnosis technology, thereby having a desirable application prospect.

Although some embodiments of the present disclosure have been described in detail through examples, those skilled in the art should understand that above-mentioned examples are provided for illustration only and not for the purpose of limiting the scope of the disclosure. Those skilled in the art should understand that modifications may be made to above-mentioned embodiments without departing from the scope and spirit of the present disclosure. The scope of the present disclosure may be defined by appended claims.

The invention claimed is:

1. A reagent kit for detecting renal cell carcinoma, comprising:
a set of primer-probe mixes for detecting miRNAs in exosomes, wherein:
the set of primer-probe mixes includes a reverse transcription primer R-23b for a specific reverse transcription miR-23b-5p target, a universal forward primer Ge—F for fluorescent PCR (polymerase chain reaction) detection, a specific reverse primer 23b-R, and a specific probe 23b-P; a reverse transcription primer R-34c for a specific reverse transcription miR-34c-5p target, a universal forward primer Ge—F for fluorescent PCR detection, a specific reverse primer 34c-R, and a specific probe 34c-P; a reverse transcription primer R-210 for a specific reverse transcription miR-210-3p target, a universal forward primer Ge—F for fluorescent PCR detection, a specific reverse primer 210-R, and a specific probe 210-P; and a reverse transcription primer R-508 for a specific reverse transcription miR-508-3p target, a universal forward primer Ge—F for fluorescent PCR detection, a specific reverse primer 508-R, and a specific probe 508-P; wherein the set of primer-probe mixes includes:

```
R-23b (SEQ ID NO: 1):
5'-GTGCTAAGCACAGCAGGGTCCGAGGTATTCGCTGTGCTTA

GCACGTGGTA-3';

R-34c (SEQ ID NO: 2):
5'-CACGATTCGTGAGCAGGGTCCGAGGTATTCGCTCACGAAT

CGTGGCAATC-3';

R-210 (SEQ ID NO: 3):
5'-TGCATCAGATGTGCAGGGTCCGAGGTATTCGCACATCTGA

TGCATCAGCC-3';

R-508 (SEQ ID NO: 4):
5-CGTACAGTCCAGGCAGGGTCCGAGGTATTCGCCTGGACTGT

ACGTCTACTC-3';

Ge-F (SEQ ID NO: 5):
5'-GCAGGGTCCGAGGTATTC-3';

23b-R (SEQ ID NO: 6):
5'-CATCACATTGCCAGGGAT-3';

34c-R (SEQ ID NO: 7):
5'-GCAGGCAGTGTAGTTAGCT-3';

210-R (SEQ ID NO: 8):
5'-GGCTGTGCGTGTGACAGC-3';

508-R (SEQ ID NO: 9):
5'-GCTGATTGTAGCCTTTTG-3';

23b-P (SEQ ID NO: 10):
5'FAM-ACCACGTGCTAAGCACAG-MGB 3';

34c-P (SEQ ID NO: 11):
5'VIC-GATTGCCACGATTCGTGAGC-MGB3';

210-P (SEQ ID NO: 12):
5'ROX-GCTGATGCATCAGATGTG-MGB 3';
and

508-P (SEQ ID NO: 13):
5'CY5-AGTAGACGTACAGTCCAGG-MGB 3'.
```

2. The reagent kit according to claim 1, wherein:
the reagent kit includes a reverse transcription reagent, a primer-probe mix reagent containing the set of primer-probe mixes, a PCR reagent, a positive control, and a negative control for the combined detection measurement.

3. The reagent kit according to claim 2, wherein:
a composition of the primer-probe mix reagent includes 1 µM Ge—F, 0.25 µM 23b-R, 0.25 µM 34c-R, 0.25 µM 210-R, 0.25 µM 508-R, 0.25 µM 23b-P, 0.25 µM 34c-P, 0.25 µM 210-P, and 0.25UM 508-P.

4. A method for detecting renal cell carcinoma, comprising:
preparing a reagent kit for detecting renal cell carcinoma, wherein the reagent kit includes:
a set of primer-probe mixes for detecting miRNAs in exosomes, wherein:
the set of primer-probe mixes includes a reverse transcription primer R-23b for a specific reverse transcription miR-23b-5p target, a universal forward primer Ge—F for fluorescent PCR (polymerase chain reaction) detection, a specific reverse primer 23b-R, and a specific probe 23b-P; a reverse transcription primer R-34c for a specific reverse transcription miR-34c-5p target, a universal forward primer Ge—F for fluorescent PCR detection, a specific reverse primer 34c-R, and a specific probe 34c-P; a reverse transcription primer R-210 for a specific reverse transcription miR-210-3p target, a universal forward primer Ge—F for fluorescent PCR detection, a specific reverse primer 210-R, and a specific probe 210-P; and a reverse transcription primer R-508 for a specific reverse transcription miR-508-3p target, a universal forward primer Ge—F for fluorescent PCR detection, a specific reverse primer 508-R, and a specific probe 508-P, wherein the set of primer-probe mixes includes:

```
R-23b (SEQ ID NO: 1):
5'-GTGCTAAGCACAGCAGGGTCCGAGGTATTCGCTGTGCTTA

GCACGTGGTA-3';

R-34c (SEQ ID NO: 2):
5'-CACGATTCGTGAGCAGGGTCCGAGGTATTCGCTCACGAAT

CGTGGCAATC-3';

R-210 (SEQ ID NO: 3):
5'-TGCATCAGATGTGCAGGGTCCGAGGTATTCGCACATCTGA

TGCATCAGCC-3';

R-508 (SEQ ID NO: 4):
5-CGTACAGTCCAGGCAGGGTCCGAGGTATTCGCCTGGACTGT

ACGTCTACTC-3';

Ge-F (SEQ ID NO: 5):
5'-GCAGGGTCCGAGGTATTC-3';

23b-R (SEQ ID NO: 6):
5'-CATCACATTGCCAGGGAT-3';

34c-R (SEQ ID NO: 7):
5'-GCAGGCAGTGTAGTTAGCT-3';

210-R (SEQ ID NO: 8):
5'-GGCTGTGCGTGTGACAGC-3';

508-R (SEQ ID NO: 9):
5'-GCTGATTGTAGCCTTTTG-3';

23b-P (SEQ ID NO: 10):
5'FAM-ACCACGTGCTAAGCACAG-MGB 3';

34c-P (SEQ ID NO: 11):
5'VIC-GATTGCCACGATTCGTGAGC-MGB3';

210-P (SEQ ID NO: 12):
5'ROX-GCTGATGCATCAGATGTG-MGB 3';
and

508-P (SEQ ID NO: 13):
5'CY5-AGTAGACGTACAGTCCAGG-MGB 3';
``` detecting exosomal miRNA targets including miR-23b-5p, miR-34c-5p, miR-210-3p and miR-508-3p in a single tube with the reagent kit by performing reverse transcription and PCR for a urine sample of a subject for an miR-23b-5p detection, an miR-34c-5p detection, an miR-210-3p detection, and an miR-508-3p detection, thereby providing a Ct value of the miR-23b-5p detection as A, a Ct value of the miR-34c-5p detection as B, a Ct value of the miR-210-3p detection as C, and a Ct value of miR-508-3p detection as D;

obtaining a Mi-Score wherein Mi-Score=1/[1+exp(−z)], while z=52.3−0.18*A−0.33*B−0.79*C−0.76*D; and determining a risk level of the subject based on the Mi-Score for the renal cell carcinoma.

5. The method according to claim 4, wherein when the Mi-Score is greater than 0.65, the subject has a higher risk of renal cancer, and when the Mi-Score is less than 0.65, the subject has a lower risk of renal cancer.

\* \* \* \* \*

SEQUENCE LISTING

<160> NUMBER OF SEQ ID NOS: 13

<210> SEQ ID NO 1
<211> LENGTH: 50
<212> TYPE: DNA
<213> ORGANISM: Artificial Sequence
<220> FEATURE:
<223> OTHER INFORMATION: Synthetic construct

<400> SEQUENCE: 1

```
gtgctaagca cagcagggtc cgaggtattc gctgtgctta gcacgtggta           50

<210> SEQ ID NO 2
<211> LENGTH: 50
<212> TYPE: DNA
<213> ORGANISM: Artificial Sequence
<220> FEATURE:
<223> OTHER INFORMATION: Synthetic construct

<400> SEQUENCE: 2
cacgattcgt gagcagggtc cgaggtattc gctcacgaat cgtggcaatc           50

<210> SEQ ID NO 3
<211> LENGTH: 50
<212> TYPE: DNA
<213> ORGANISM: Artificial Sequence
<220> FEATURE:
<223> OTHER INFORMATION: Synthetic construct

<400> SEQUENCE: 3
tgcatcagat gtgcagggtc cgaggtattc gcacatctga tgcatcagcc           50

<210> SEQ ID NO 4
<211> LENGTH: 51
<212> TYPE: DNA
<213> ORGANISM: Artificial Sequence
<220> FEATURE:
<223> OTHER INFORMATION: Synthetic construct

<400> SEQUENCE: 4
cgtacagtcc aggcagggtc cgaggtattc gcctggactg tacgtctact c         51

<210> SEQ ID NO 5
<211> LENGTH: 18
<212> TYPE: DNA
<213> ORGANISM: Artificial Sequence
<220> FEATURE:
<223> OTHER INFORMATION: Synthetic construct

<400> SEQUENCE: 5
gcagggtccg aggtattc                                              18

<210> SEQ ID NO 6
<211> LENGTH: 18
<212> TYPE: DNA
<213> ORGANISM: Artificial Sequence
<220> FEATURE:
<223> OTHER INFORMATION: Synthetic construct

<400> SEQUENCE: 6
catcacattg ccagggat                                              18

<210> SEQ ID NO 7
<211> LENGTH: 19
<212> TYPE: DNA
<213> ORGANISM: Artificial Sequence
<220> FEATURE:
<223> OTHER INFORMATION: Synthetic construct

<400> SEQUENCE: 7
gcaggcagtg tagttagct                                             19

<210> SEQ ID NO 8
<211> LENGTH: 18
<212> TYPE: DNA
```

```
<213> ORGANISM: Artificial Sequence
<220> FEATURE:
<223> OTHER INFORMATION: Synthetic construct

<400> SEQUENCE: 8
ggctgtgcgt gtgacagc                                                 18

<210> SEQ ID NO 9
<211> LENGTH: 18
<212> TYPE: DNA
<213> ORGANISM: Artificial Sequence
<220> FEATURE:
<223> OTHER INFORMATION: Synthetic construct

<400> SEQUENCE: 9
gctgattgta gccttttg                                                 18

<210> SEQ ID NO 10
<211> LENGTH: 18
<212> TYPE: DNA
<213> ORGANISM: Artificial Sequence
<220> FEATURE:
<223> OTHER INFORMATION: Synthetic construct

<400> SEQUENCE: 10
accacgtgct aagcacag                                                 18

<210> SEQ ID NO 11
<211> LENGTH: 20
<212> TYPE: DNA
<213> ORGANISM: Artificial Sequence
<220> FEATURE:
<223> OTHER INFORMATION: Synthetic construct

<400> SEQUENCE: 11
gattgccacg attcgtgagc                                               20

<210> SEQ ID NO 12
<211> LENGTH: 18
<212> TYPE: DNA
<213> ORGANISM: Artificial Sequence
<220> FEATURE:
<223> OTHER INFORMATION: Synthetic construct

<400> SEQUENCE: 12
gctgatgcat cagatgtg                                                 18

<210> SEQ ID NO 13
<211> LENGTH: 19
<212> TYPE: DNA
<213> ORGANISM: Artificial Sequence
<220> FEATURE:
<223> OTHER INFORMATION: Synthetic construct

<400> SEQUENCE: 13
agtagacgta cagtccagg                                                19
```